United States Patent [19]

Shaw

[11] Patent Number: 5,672,512
[45] Date of Patent: Sep. 30, 1997

[54] CHAIN INCUBATOR/CONVEYOR AND METHOD OF USE

[75] Inventor: James D. Shaw, Hilton, N.Y.

[73] Assignee: Johnson & Johnson Clinical Diagnostics, Inc., Rochester, N.Y.

[21] Appl. No.: 599,901

[22] Filed: Feb. 12, 1996

Related U.S. Application Data

[60] Continuation-in-part of Ser. No. 504,170, Jul. 19, 1995, abandoned, which is a division of Ser. No. 354,683, Dec. 12, 1994, abandoned.

[51] Int. Cl.⁶ .................................................. G01N 35/00
[52] U.S. Cl. .................. 436/46; 436/43; 436/47; 436/48; 422/63; 422/65; 422/66; 422/104; 198/801; 198/860.3; 198/952
[58] Field of Search .......................... 422/63, 65, 66, 422/67, 103, 104; 436/43, 44, 46–48; 198/801, 860.3, 952

[56] References Cited

U.S. PATENT DOCUMENTS

| | | | |
|---|---|---|---|
| 1,736,866 | 11/1929 | Wagner et al. | 198/801 |
| 1,995,273 | 3/1935 | Dohrwardt | 198/801 |
| 3,575,692 | 4/1971 | Gilford | 422/65 |
| 4,058,908 | 11/1977 | Weber | 34/149 |
| 4,119,381 | 10/1978 | Muka et al. | 356/244 |
| 4,219,529 | 8/1980 | Tersteeg et al. | 422/65 |
| 4,641,740 | 2/1987 | Grecksch et al. | 198/487.1 |
| 4,857,272 | 8/1989 | Sugaya | 422/65 |
| 5,149,654 | 9/1992 | Gross et al. | 435/287 |
| 5,339,537 | 8/1994 | Kuster | 34/612 |

OTHER PUBLICATIONS

"Storage Elevator", Research Disclosure, May 1990, Article No. 31372, pp. 412–413.

*Primary Examiner*—Long V. Le
*Attorney, Agent, or Firm*—Dana M. Schmidt

[57] ABSTRACT

A chain incubator or conveyor, and method of use in an analyzer, wherein an endless chain is formed of repeating members and each comprising a link, element support, a cover, and means for biasing the cover onto the support with an article such as a test element between them. The members are linked together by a pair of pivot pins, and the chain is engaged by a drive sprocket and an idler sprocket.

18 Claims, 6 Drawing Sheets

CHAIN INCUBATOR/CONVEYOR AND METHOD OF USE

This is a continuation-in-part of application Ser. No. 08/504,170, filed Jul. 19, 1995, now abandoned, which is a divisional of application Ser. No. 08/354,683, filed Dec. 12, 1994, now abandoned.

FIELD OF THE INVENTION

The invention relates to a novel incubator or conveyor of particular use in an analyzer, to achieve improved throughput.

BACKGROUND OF THE INVENTION

Incubators of chemical analyzers come in various forms, the most common of which is a horizontally disposed platform, such as a rotor, on which test elements are placed at stations and stored at controlled temperatures until they are ready for reading. Such rotor incubators do at least minimize the time needed to access any station, given that the stations are in the form of an endless loop that can be accessed without going all the way to an "end". Minimal access time is an important factor in high throughput.

The problem however is that such a construction is limited nevertheless as to throughput. Although more stations can be added by enlarging the circumference, it is not usually feasible to add concentric rows of stations inside the outermost row. One approach is to add another rotor, thereby generally doubling the throughput. However, if a 60 cm diameter rotor has only 54 stations around its circumference, this means that 2827 cm² are occupied by the footprint of the rotor to handle only 54 test elements at a time, or twice this when using two stacked rotors. The problem then of the invention has been to provide a more useful design in an endless loop form that occupies the same approximate volume of a 2827 cm² or less area, but which has at least twice as many stations thereon.

U.S. Pat. No. 4,119,381 does describe an incubator using a rotor in which the flow of the stations and the supporting platforms is in the vertical, rather than the horizontal, dimension. However, the incubator of that patent is functionally equivalent to rotors now disposed horizontally, which is simply rotated 90° to move through a vertical plane rather than a horizontal plane. By retaining the rotor format, it is limited in its packing density by the same limitations provided in horizontally-disposed rotors.

RELATED APPLICATIONS

Commonly owned U.S. Ser. No. 08/236,908 filed by Muszak on Apr. 29, 1994 entitled Twin Rotor Elevator Assay describes an elevator, now U.S. Pat. No. 5,419,871, FIG. 15, for moving plural test elements to rotor incubators stacked at various levels. Although it is not shown, at a given time there may be test elements disposed in two elevator stations at a given time. However, the stations are not stacked vertically together, nor does this provide the advantages of the instant invention.

SUMMARY OF THE INVENTION

I have constructed an incubator/conveyor and a method of processing test elements that solves the noted problems.

More specifically, in accord with one aspect of the invention, there is provided an incubator for a chemical analyzer, comprising a plurality of test element supports vertically joined together in a stacked assembly, the assembly comprising at least a pair of opposed pivot points attached to each of the supports and at least one pivot pin, the pivot pin passing through and joining a pivot point of one support to a pivot point of an adjacent support, and means for moving the stack in a vertical direction.

In accord with another aspect of the invention, there is provided in an endless chain conveyor comprising a plurality of links pivotally connected to each other at opposite ends by pins, a drive sprocket and an idler sprocket each having teeth spaced and spaced to engage the links, and an article support projecting from each of the links. The conveyor is improved in that the conveyor further includes for each of the links, a cover movably positioned over each support, and biasing means for removably biasing the cover against each support, and wherein the sprockets are disposed one above the other so that the supports are oriented generally horizontally except when their respective links engage the sprockets.

In accord with yet another aspect of the invention, there is provided an incubator for a chemical analyzer, comprising a plurality of test element supports vertically joined together in a stacked assembly with each support disposed horizontally, at least some of each of the supports occupying a particular horizontal position at any one time, and moving means for vertically moving such some supports out of the horizontal position into the next adjacent horizontal position previously occupied by an adjacent support.

In accord with still another aspect of the invention, there is provided a method of processing a test element, comprising dispensing an aliquot of patient sample into a selected test element for a particular assay, pushing the test element with the aliquot onto a support of an incubator, at the first location, raising or lowering the support from the first location to a second location removed from the first location, pushing the test element from the second portion directly into a read station, and detecting the result produced by the patient sample in the test element at the read station.

In accord with still a further aspect of the invention, there is provided a method of efficiently loading slide test elements onto an incubator comprising a continuous series of slide test element supports joined together for movement past a loading station which may or may not have a slide test element present for loading and means for moving the supports incrementally in a selected direction past the loading station, the joined supports and the moving means defining a flexible and variable path of travel for the supports, the method comprising the steps of alternately moving the supports past the loading station and loading any slide test element presented by the station, from the station onto a support aligned opposite the station if the aligned support is empty, and in the event no slide test element is presented by the station to a given empty support prior to the empty support moving past the station, then distorting the flexible path if a slide test element is presented at the station immediately after the empty support passes, so that the empty support is repositioned and aligned with the station now presenting a slide test element.

In accord with yet a further aspect of the invention, there is provided an incubator comprising a continuous series of slide test element supports joined together for movement past a loading station which may or may not have a slide test element present for loading and means for moving the supports incrementally in a selected direction past the loading station. The incubator is improved in that the supports are flexibly joined together and wherein the moving means define a path of travel of the joined supports that is variable in shape, and further including a linear actuator for pushing or pulling the joined supports to vary the shape of said travel path sufficiently to push or pull a slide test element support that has passed or is passing the loading station in the selected direction, back into position in which it is opposite the loading station and ready to receive a slide test element from the loading station.

Accordingly, it is an advantageous feature of the invention that an increased-throughput incubator is provided by linking incubator supports closely together with a flow path in the vertical dimension rather than the horizontal dimension that has been the hallmark of conventional incubators.

It is a related advantageous feature that this is achieved by constructing the incubator in the form of an endless chain conveyor.

Other advantageous features will become apparent in the "Detailed Description" which follows, when read in light of the attached drawings.

DESCRIPTION OF THE PREFERRED EMBODIMENTS

The invention is described in connection with certain preferred embodiments, in which the chain incubator, or conveyor, is driven by a tooth sprocket and idler sprocket of a particular design, disposed directly one above the other, wherein each test element support of the incubator has a cover of a particular design held in place by a torsion bar spring clip, the incubator being used with two separate pusher blades, one to load and one to unload, at two different locations. In addition, the incubator of the invention is useful regardless of the design of the drive and idler sprockets and of their relative positions; regardless of the shape or use of a cover and the kind of spring holding the cover in place; and regardless of the number, position or kind of pusher blades used to load and unload the incubator.

Figure 1:
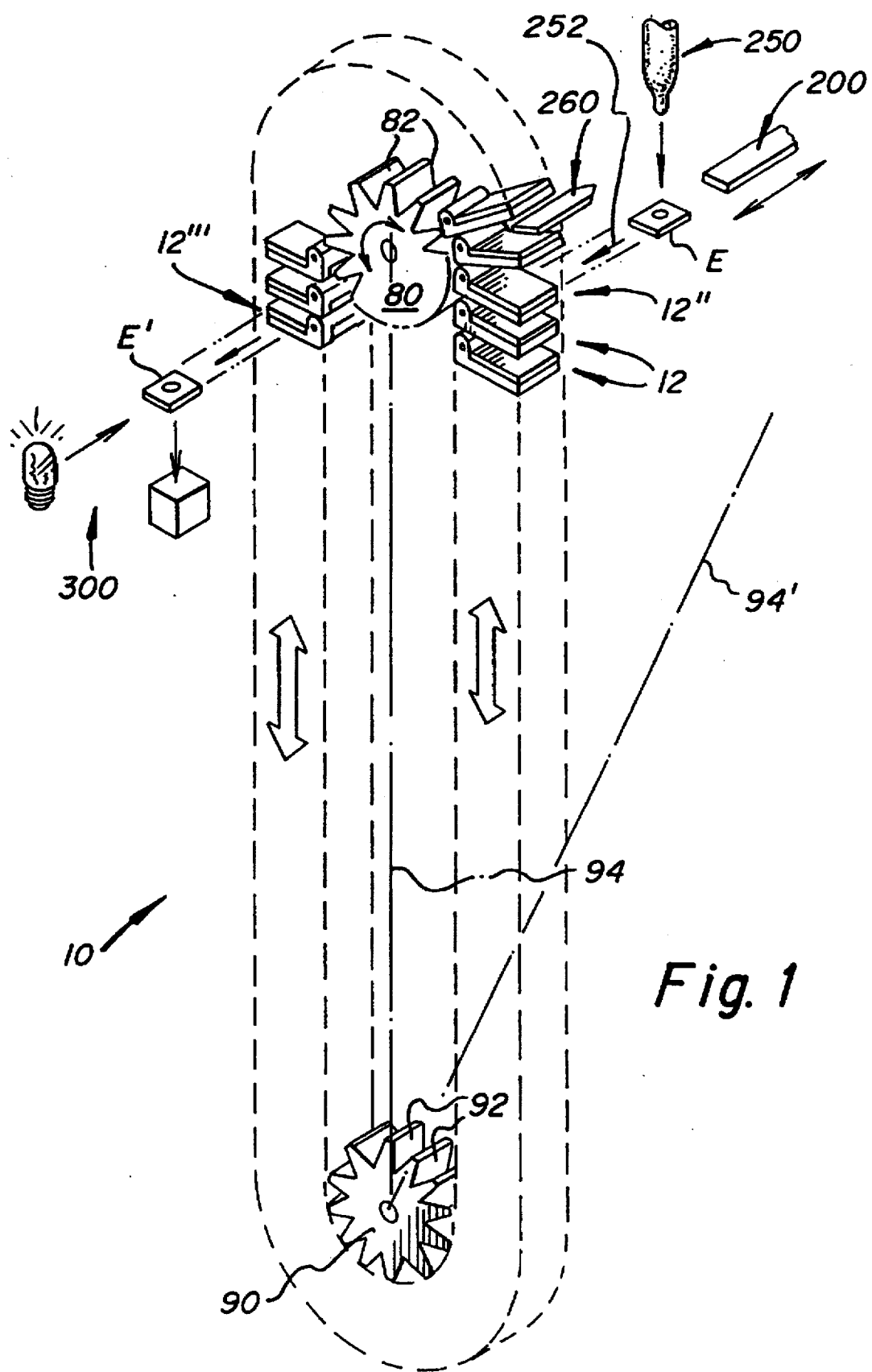
FIG. 1 is a fragmentary isometric view of a chain incubator constructed in accordance with the invention, and showing portions of an analyzer with which the incubator is used.
Figure 3:
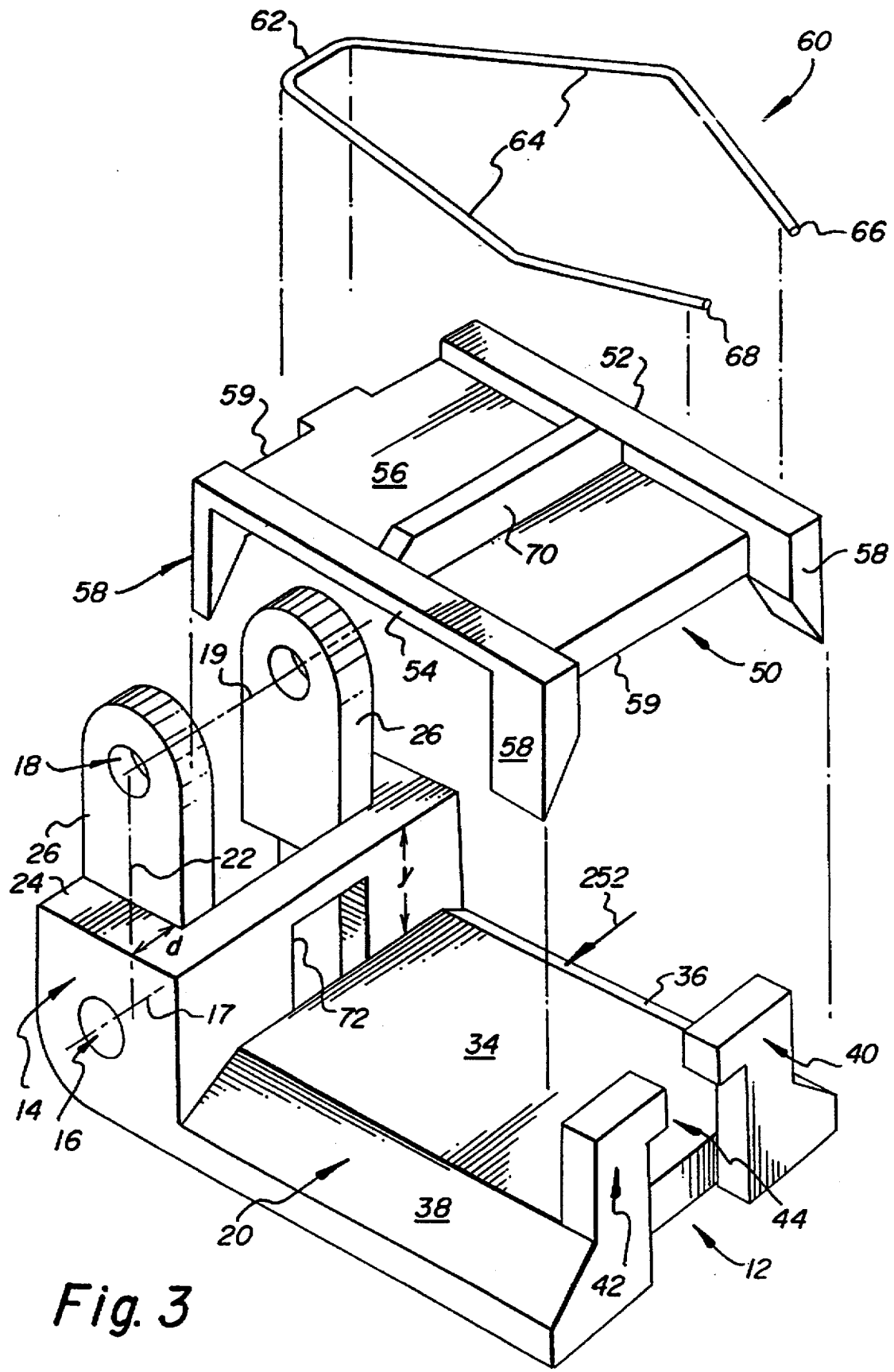
FIG. 3 is an exploded isometric view of a single member of the chain of the invention, the pin and roller (of FIG. 2) being removed for clarity.

AS shown in FIG. 1, the incubator or conveyor of the invention comprises an endless chain 10 made up of a plurality of members 12, each having two portions, FIG. 3, a link portion 14 extending between two pivot points 16 and 18 defined as pivot apertures extending along axes 12 and 19, respectively, and a test element support portion 20 extending generally perpendicularly from a line 22 drawn between the pivot axes of points 16 and 18. A cover 50 is biased onto support portion 20 by a spring 60 as described hereinafter.

Figure 4:
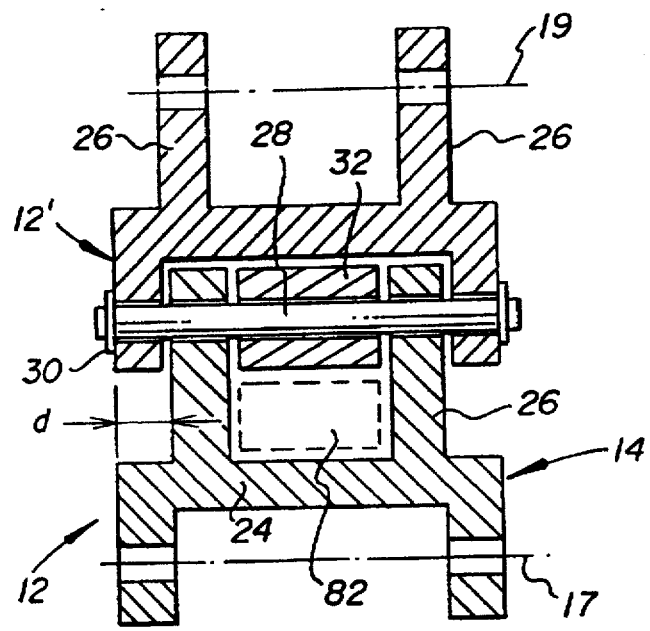
FIG. 4 is a section view of two members of the chain, taken generally through the plane IV—IV—IV—IV of FIG. 2.

Preferably, link portion 14 comprises a shoulder 24 through which the paired apertures of axis 17 extend, and a pair of ears 26 rising from the shoulder. Ears 26 are each moved inwardly a distance "d", to define an offset for receiving the shoulder of the next adjacent member 12', FIG. 4. The paired apertures of pivot axis 19 are provided in ears 26. Pivot pins 28 connecting members 12 and 12', FIG. 4, are then inserted through the apertures of pivot axes 17 and 19 to pivotally connect the chain together. Retaining rings 30 hold pins 28 in place, as is conventional. A roller 32 is disposed on pins 28 to give rolling contact with the sprockets, described below. The result of this construction is to join a pivot point of one support 20 at one of the ends of link 14 of that support, to the pivot point of an adjacent support 20 at the other of the ends of its link 14.

Figure 2:
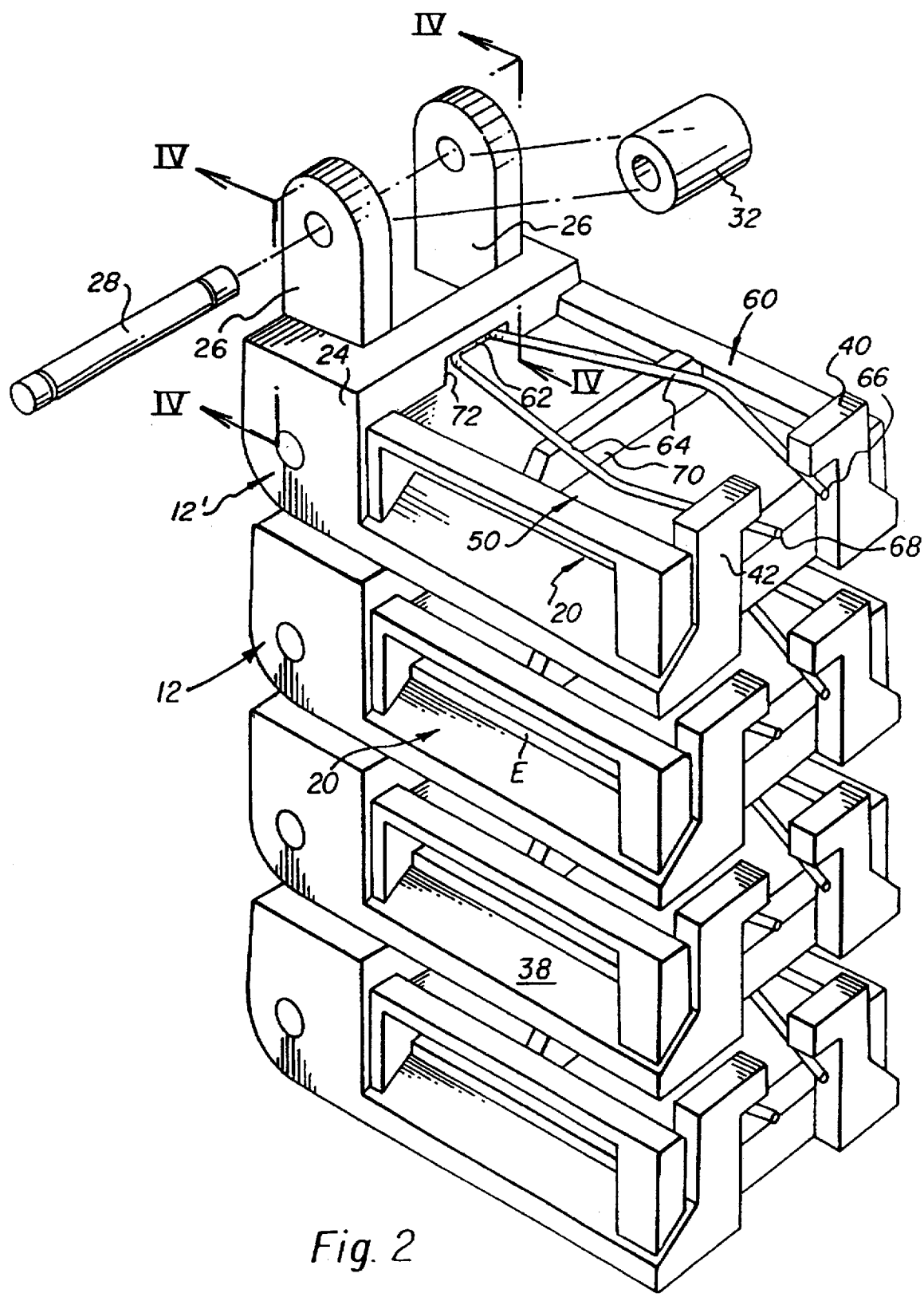
FIG. 2 is an enlarged, partially exploded fragmentary isometric view similar to that of FIG. 1, illustrating further detail.

Preferably, support portion 20, FIG. 3, is disposed a distance "y" below shoulder 24 to receive both cover 50 and a test element E between cover 50 and support portion 20, FIG. 2. Most preferably, FIG. 3, support portion 20 comprises surface 34 that extends generally horizontally except when members 12 and 12' move around the sprockets, and opposite camming edges 36 and 38 that act to guide a test element onto or off of surface 34. Additionally, as shown more clearly for member 12 in FIG. 2, when a test element E is in place, edges 36 and 38 project beyond the outermost edge of element E, thus providing good thermal contact between support portion 20 and the heated air flowing around the chain incubator, FIG. 6. Retaining fingers 40, 42 extend, FIG. 3, upward from surface 34 to help confine cover 50. An air flow gap 44 is provided under and between fingers 40, 42.

Representative examples for the dimensions "d" and "y" discussed above are, 0.3 cm and 0.5 cm, respectively.

Figure 5:
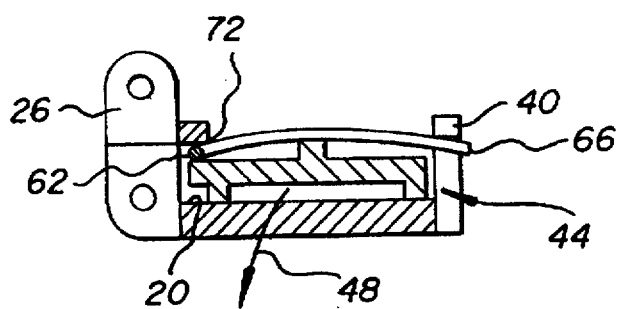
FIG. 5 is an elevational view in section of the assembled member of FIG. 3.

For a similar reason, FIG. 3, cover 50 is constructed to be relatively open at opposite edges 52, 54. That is, cover 50 comprises a top panel 56 with depending legs 58 that leave open the front and back faces 59 as well as at edges 52 and 54. This open construction of cover 50 as it sits on support portion 20, FIG. 5, along with the air flow through gap 44, provides for rapid air flow, as shown by arrow 48, when no test element is present, a decided advantage in removing residual gases possibly produced by the last test element to have been supported.

To releasibly clamp or bias cover 50 in place onto support portion 20, a spring 60 is provided, preferably in the form of a U-shaped torsion bar. That is, spring 60 has a base 62 and legs 64 which extend from base 62 to terminate in ends 66, 68. Legs 64 are slightly bowed so as to extend over a biasing ridge 70 provided in panel 56. As is more clearly shown in FIGS. 2 and 5, base 62 fits into the top part of aperture 72 provided for that purpose in shoulder 24 above support portion 20, while ends 66, 68 slip under and are held by fingers 40, 42.

It will be readily apparent from the preceding that an advantage of the invention is that all of members 12 (and 12') are substantially identical to each in construction, and thus are interchangeable. Furthermore, the length of the chain is greatly variable. Because of the close stacking of the members 12 together, with a minimum footprint, the throughput is greatly increased for just a single incubator. Still further, the reduced footprint means that more than one incubator can be used per analyzer, to further increase throughput.

To move the endless incubator or conveyor so created as described above, and preferably in vertical directions (up and down), a drive sprocket 80 and an idler sprocket 90 are provided, FIG. 1, that engage link portions 14 in members 12 and 12' of incubator 10. Such sprockets are conventional, and comprise a toothed wheel the teeth 82 and 92, respectively, of which are shaped and spaced so as to fit within the space provided shown in phantom, FIG. 4, between roller 32 and shoulder 24. Sprocket 80 is driven by any conventional motor and drive shaft (not shown), and sprocket 90 is journaled to freely rotate (not shown). To minimize the foot print of the incubator, sprocket 80 is preferably disposed directly above sprocket 90, FIG. 1, so that a line 94 between them is substantially vertical. Alternatively, however, the sprockets can be disposed so that they are not vertically aligned, e.g., line 94 can be inclined to the vertical in either direction, as suggested by 94'.

Figure 6:
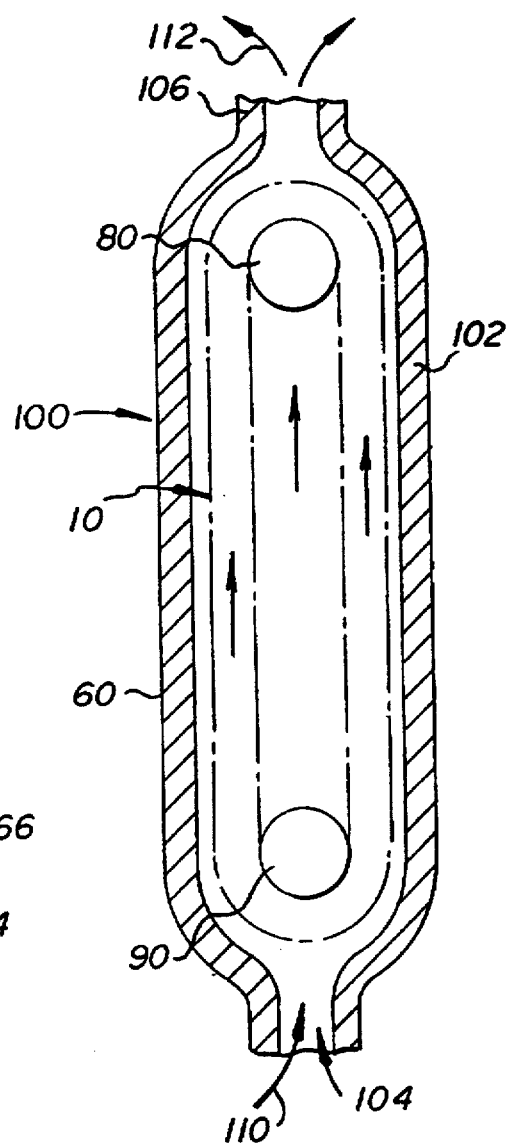
FIG. 6 is a fragmentary elevational view in section of the insulated enclosure of the incubator.

Any incubator needs a source of thermal control, and this is achieved for incubator 10 preferably by an insulated enclosure 100, FIG. 6. The enclosure comprises a housing 102 completely surrounding chain incubator 10, except for an air inlet 104 and an air exit 106. Inlet 104 is preferably directly below sprocket 90 whereas exit 106 is directly above sprocket 80, so that air flows as indicated by arrows 110, 112. The heating of the air flowing in, arrows 110, is done by any conventional heater, not shown, upstream of incubator 10.

To load and unload incubator 10, FIG. 1, at least one pusher blade 260 is provided, to cooperate with an appropriately positioned aperture (not shown) in the enclosure described above extending around incubator 10. Such a pusher blade can be rigid, as taught for example in U.S. Pat. No. 4,512,952, or it can be flexible, as taught for example in U.S. Pat. No. 5,330,716. It pushes test element E from a conventional source of test elements, not shown, x to and from a liquid-dispensing station 250 shown schematically, directly into chain incubator, arrow 252, via the opening at edge 52, FIG. 3, provided between cover 50 and support 20. This same pusher blade can then be used at the same location to remove element E after it is incubated, but preferably a second pusher blade 260, FIG. 1, is disposed at a different location, with appropriate slots in the enclosure (not shown) to eject an element E' directly into a read station 300 shown schematically.

The use of the incubator/conveyor of the invention will be readily apparent from the preceding. That is, FIG. 1, drive sprocket 80 is effective to force chain incubator/conveyor 10 to move so that supports 20 extend out generally horizontally, and displace each other vertically, either up or down, depending on the drive direction of sprocket 80. Thus, sprocket 80 and incubator 10 are effective to move, FIG. 2, support 20 of chain member 12, and element E, vertically upward, for example, to occupy the horizontal position previously occupied by support 20 of member 12'.

In sequence, then, an aliquot of patient sample is dispensed at station 250 onto test element E, and that element is then pushed onto support 20 of chain member 12", under its cover 50. Member 12" is then raised or lowered by drive sprocket 80 to subsequent locations above or below that currently shown, until it is completely incubated. Then, member 12" is preferably located at the position shown for member 12''', where blade 260 is activated to push the element, shown as element E', directly into read station 300, where the result produced by the patient sample is detected. (The precise positioning of stations 250 and blade 260 vis-a-vis drive sprocket 80 is arbitrary and depends on the location of other analyzer features, as will be understood.)

A chain incubator has a further advantage over other forms of continuous or endless supports for slide test elements. That is, it is inherently flexible due to the links' ability to pivot with respect to the adjacent links. This flexibility means that the path of travel of the chain can be changed or distorted, if the chain is properly mounted on its moving means. In contrast, such flexibility does not exist in the rigid rotor supports common in the prior art.

Such a change or distortion in the path of travel becomes important when the chain incubator is used in an analyzer having other incubators handling other kinds of slide test elements besides those handled by the chain incubator. Thus, the rest of the analyzer (not shown) preferably includes such other, conventional incubators such as rotors. In such an arrangement, the chain incubator can handle, for example, end-point chemistries, whereas the others handle, e.g., rate and potentiometric chemistries, as is known.

The need to change the path of travel of the chain incubator arises more specifically from the fact that, in an analyzer having such plural incubators, slide test elements presented to the chain incubator will be presented with a random timing. That is, slide test elements of all three types noted above will be "spotted" with test sample in a random order, instead of all end-point chemistries, for example, going together. As a result, the slide test elements will appear on the distributor presenting test elements to the chain incubator, also in random order, even though only the end-point chemistries, in this example, can be loaded onto the chain incubator. Thus, half the time, if the end-point test elements are only half of the tests, the test element on the distributor will have to pass up the chain incubator. This means that an empty test element support on the chain will go past the distributor half the time, without the feature hereinafter discussed. Because the timing of the end-point test elements' distribution on the distributor is in fact random as noted above, it is otherwise impossible to create the chain incubator with link lengths that are adjusted to accommodate "skips" representing non-acceptable test element types.

Figure 7:
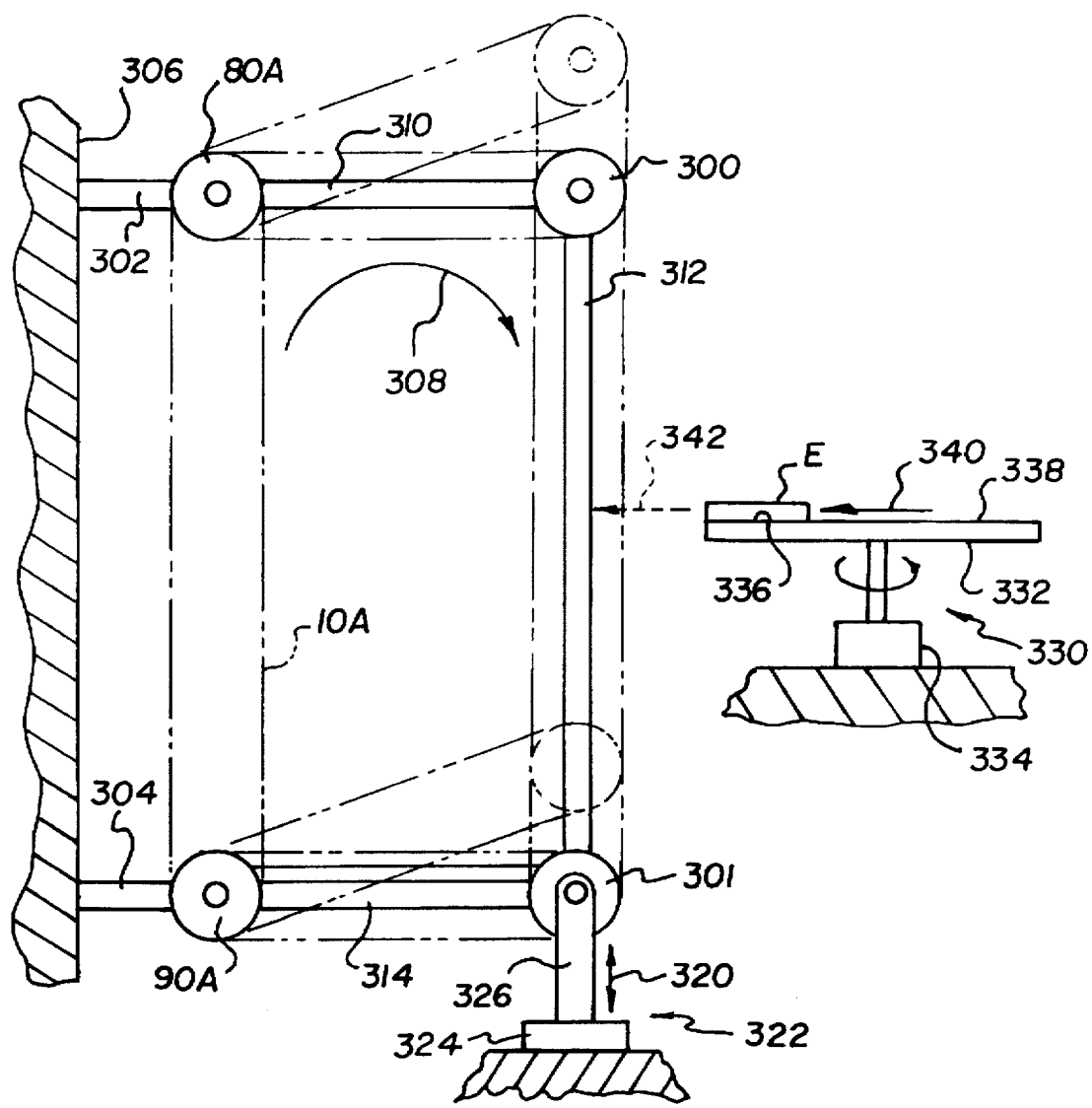
FIG. 7 is a fragmentary elevational view partly in section, illustrating yet another embodiment of the invention.

Thus, in FIG. 7, there is shown a mechanism by which the flexible path of travel of the chain incubator can be altered or distorted, to solve the problem just noted. Before discussing the details, the "use" for such distortion or altering is to allow the loading station to "catch-up" with an empty incubator support that has already passed, by signaling to an actuator that alters the path of the chain, to bring the empty support back into alignment with the loading station, all without reversing the direction the chain is being driven. (Parts similar to those previously described bear the same reference numeral, to which the distinguishing suffix A is appended.)

As to the details, the incubator of the invention comprises an endless or continuous series of members that include slide test element supports all linked together in the manner described above in connection with FIGS. 1–5. The chain and conveyor so formed is designated by parallel dashed lines 10A. This chain or conveyor is moved by means which preferably include a drive sprocket 80A, and idler sprocket 90A and two additional idler sprockets 300, 301. Sprockets 80A and 90A are journalled to brackets 302 and 304, respectively, which are fixed in place on support surface 306 of the analyzer. The entire chain is driven in a selected direction, for example, the clockwise direction of arrow 308.

Sprockets 300,301 are in turn journalled at the junction of two bars 310,312 or 312,314 that are pivotally mounted on brackets 302 and 304 to form a conventional four-bar linkage. (Fixed support 306 forms the fourth "bar" in the linkage.) As such, then, chain 10A is subject to a distorted or alterable flexible path of travel, shown in phantom, simply by pushing or pulling, arrow 320, on the four-bar linkage. The pushing or pulling is achieved preferably via a linear actuator 322, which preferably comprises a solenoid 324 fixed to the analyzer, using rod 326 that is journalled to the pivot connection of bars 312 and 314. (Alternatively, linear actuator 322 can be connected instead to the junction of bars 310 and 312.)

The incubator travels past a loading station similarly to that shown as station 250, FIG. 1. Here, the loading station is preferably a rotatable slide test element distributor 330, comprising a rotor 332 rotated by motor 334 and comprising plural slide supports 336, 338, etc. on the rotor. (Only two supports are shown on rotor 332 for convenience.) A slide test element E is shown at support 336. A pusher blade, not shown, is effective to push slide test element E, arrow 340, into any empty support of chain 10A that is aligned with the distributor (arrow 342).

Figure 8C:
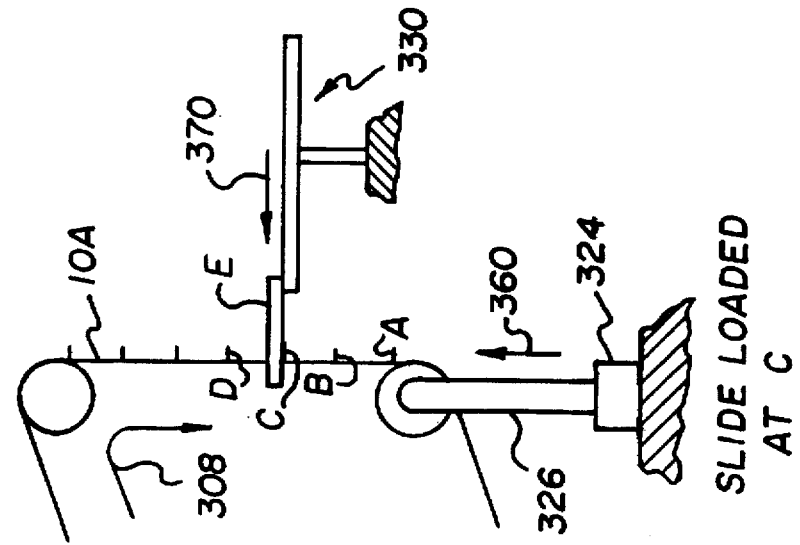
FIGS. 8A–8C are fragmentary schematic elevational view similar to FIG. 7, showing the operation of the embodiment of FIG. 7.

The operation of this embodiment is readily apparent to one skilled in the art from the above description. That is, referring especially to FIGS. 8A–8C, various members of chain 10A are incremented, arrow 308, past loading station 330, each of the adjacent slide test element supports of the chain being schematically shown as A, B, C, D, etc. As shown in FIG. 8A, each of the members or supports A-D are empty, and support C is aligned with the distributor 330 at the loading station. During loading, chain 10A is stopped from moving. However, there is no slide test element on support 336 of the rotor; hence there is no test element presented for loading. There is, however, one at support 338.

Figure 8B:
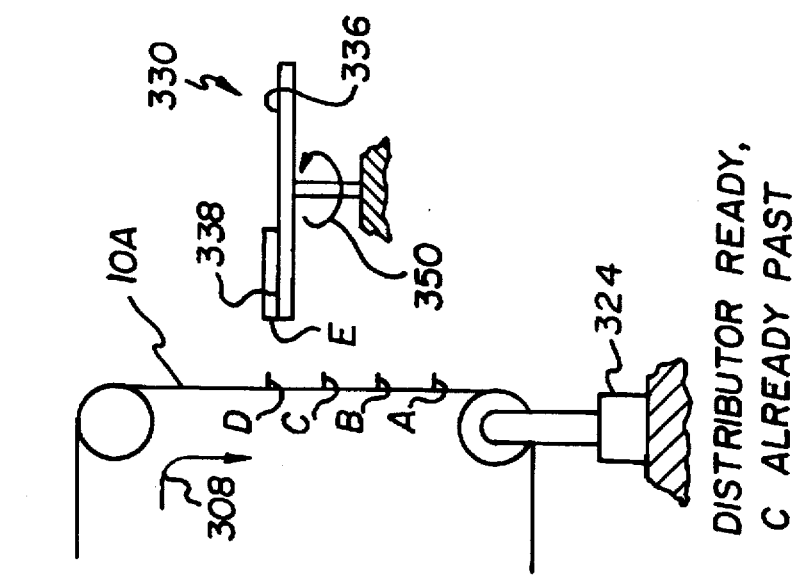
Figure 8A:
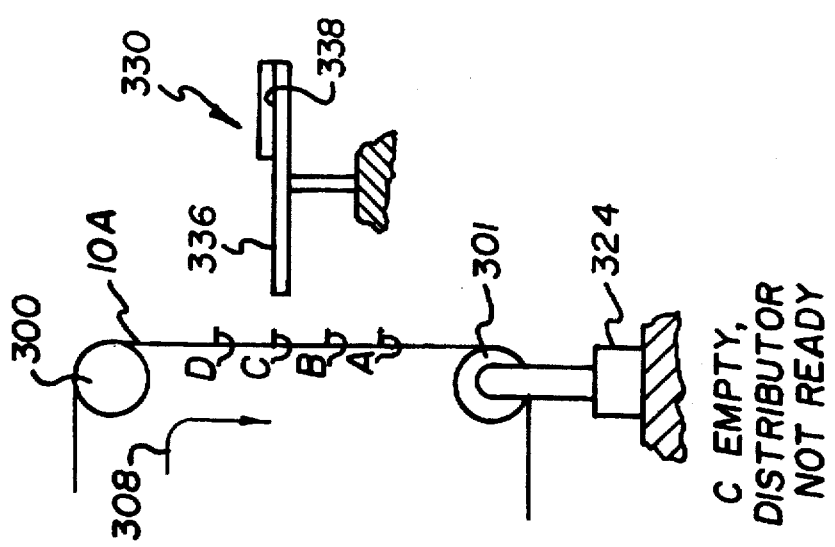

Next, FIG. 8B, chain 10A increments downward, arrow 308, bringing empty slide test element support D into alignment with distributor 330. At the same time, the distributor has rotated, arrow 350, bringing the slide test element at support 338 into presentation to chain 10A. Because test element support C is still empty, it is preferred that element E be loaded onto that support, and without causing a reversal in the chain direction, arrow 308. This occurs, FIG. 8C, by activating solenoid 324 so that rod 326 extends, arrow 360, and sprockets 300,301 move upwardly along with chain 10A, thus pushing support C back into alignment for the loading onto C of element E (arrow 370).

As a result, the chain incubator is used more efficiently than would be the case if the travel path could not be distorted.

It is, of course, not necessary that chain 10A first index in the direction of arrow 308, and then rod 326 extend upward as per arrow 360, to realign support C with the distributor. Instead, the indexing of arrow 308 and upward extension of rod 326 can be done simultaneously to keep support C aligned with the distributor for the next slide test element.

Alternatively, if chain 10A travels in a direction opposite to that of arrow 308, rod 326 is pulled by solenoid 324 to alter the shape of the path of travel of chain 10A to pull a test element support of the chain back into alignment with distributor 330.

The invention disclosed herein may be practiced in the absence of any element which is not specifically disclosed herein.

The invention has been described in detail with particular reference to preferred embodiments thereof, but it will be understood that variations and modifications can be effected within the spirit and scope of the invention.

What is claimed is:

1. A method of efficiently loading slide test elements onto an incubator comprising a continuous series of slide test element supports joined together for movement past a loading station which may or may not have a slide test element present for loading and means for moving said supports incrementally in a selected direction past said loading station, said joined supports and said moving means defining a flexible and variable path of travel for said supports, the method comprising the steps of alternately moving said supports past said loading station and loading any slide test element presented by said station, from said station onto a support aligned opposite said station if said aligned support is empty, and in the event no slide test element is presented by said station to a given empty support prior to said empty support moving past said station, then distorting said flexible path if a slide test element is presented at said station immediately after said empty support passes, so that said empty support is repositioned and aligned with said station now presenting a slide test element.

2. A method as defined in claim 1, wherein said distorting step comprises linearly pushing or pulling said joined supports out of their previous path of travel, by linearly pushing or pulling said moving means relative to said loading station.

3. In an incubator comprising a continuous series of slide test element supports joined together for movement past a loading station which may or may not have a slide test element present for loading and means for moving said supports incrementally in a selected direction past said loading station, the improvement wherein said supports are flexibly joined together and wherein said moving means define a path of travel of said joined supports that is variable in shape, and further including a linear actuator for pushing or pulling said joined supports to vary a shape of said travel path sufficiently to push or pull a slide test element support that has passed or is passing said loading station in said selected direction, back into position in which it is opposite said loading station and ready to receive a slide test element from said loading station.

4. An incubator as defined in claim 3, wherein said moving means comprise a drive sprocket and three idler sprockets, said sprockets being rotatably mounted on a four-bar linkage, one of said bars being fixed in place, and wherein said supports are linked together in a chain which is driven by said drive sprocket and rotates over said idler sprockets.

5. An incubator as defined in claim 4, wherein two of said sprockets are rotatably mounted on bars of said four-bar linkage that are free to move relative to said fixed bar, and wherein said linear actuator comprises a solenoid journalled to an idler sprocket.

6. An incubator for a chemical analyzer, comprising:

a plurality of test element supports vertically joined together in a stacked assembly with each support disposed horizontally, said assembly comprising at least a pair of opposed pivot points attached to each of said supports and at least one pivot pin, said pivot pin passing through and joining a pivot point of one support to a pivot point of an adjacent support;

moving means for moving said stack along a path in a vertical direction; and means for pushing or pulling said assembly to alter a shape of said path.

7. An incubator for a chemical analyzer, comprising:

a plurality of test element supports vertically joined together in a stacked assembly with each support disposed horizontally;

at least one of said supports occupying a particular horizontal position at any one time;

moving means for vertically moving said supports along a path, out of said horizontal position into a next adjacent horizontal position previously occupied by an adjacent support; and means for pushing or pulling said assembly to alter a shape of said path.

8. An incubator as defined in claim 7, and further including a read station adjacent to said incubator, and a pusher blade for pushing a test element from a support of the incubator directly onto said read station.

9. An incubator as defined in claim 6 and further including a read station adjacent to said incubator, and a pusher blade for pushing a test element from a support of the incubator directly onto said read station.

10. An incubator as defined in claim 9, and further including a pair of ears attached to each of said supports, each ear being spaced from the other to define a link opening, said at least one pivot pin extending through said ears at one of said pivot points, and further including a second pivot pin extending through the other of said pivot points, and further including sprockets having teeth spaced apart a distance that fits within said link opening and between each of said pivot pins of each of said supports.

11. An incubator for a chemical analyzer, comprising:

a plurality of links pivotally connected to each other at opposite ends by pins to form an endless chain conveyor with said pins having a spacing in said links, a drive sprocket and an idler sprocket each having teeth spaced apart a distance coinciding with the spacing of said pins in said links;

a test element support extending from each of said links;

a heater for maintaining said supports at a desired temperature;

means for driving said chain conveyor along a path having an alterable shape; and means for pulling or pushing said conveyor to alter said shape of said path.

12. An incubator as defined in claim 11, and further including a cover for each of said supports, each said support and said cover leaving exposed opposite edges of said support, and further including at least one pusher blade for pushing a test element onto or off of each of said supports through respective ones of said opposite side edges.

13. An endless chain conveyor comprising a plurality of links pivotally connected to each other at opposite ends by pins, a drive sprocket and an idler sprocket each having teeth spaced and shaped to engage said links, and an article support having a supporting surface projecting from each of said links, said sprockets being disposed one above the other so that said supports are oriented generally horizontally except when their respective links engage said sprockets;

a cover for each of said links, movably positioned over each said support and biasing means for removably biasing said cover against said each support, and means for driving said chain conveyor along a path having an alterable shape; and means for pushing or pulling said conveyor to alter said shape of said path.

14. A conveyor as defined in claim 13 wherein said covers, said supports and said biasing means leave exposed opposite side edges of said supports, and further including at least one pusher blade for pushing an article onto or off of each of said supports through respective ones of said opposite side edges.

15. A conveyor as defined in claim 14, and further including a second pusher blade positioned separately from said at least one pusher blade, in position for removing an article that is loaded into a support by said at least one pusher blade.

16. A conveyor as defined in claim 13, and further including a heater for maintaining said supports at a desired temperature.

17. A conveyor as defined in claim 16, and further including an insulated enclosure around said conveyor and having an air inlet and an air outlet, and wherein said heater is disposed outside of said enclosure for heating air flowing into said outlet.

18. A conveyor as defined in claim 17, wherein said inlet and outlet are aligned with a line extending between said sprockets.

* * * * *